United States Patent [19]

Bellasalma

[11] 4,036,220

[45] July 19, 1977

[54] BODY MEMBER PROTECTIVE DEVICE

[76] Inventor: Gerald John Bellasalma, 96 Park St., West Caldwell, N.J. 07006

[21] Appl. No.: 622,517

[22] Filed: Oct. 15, 1975

[51] Int. Cl.² ............................................. A61F 13/00
[52] U.S. Cl. ............................. 128/82; 128/DIG. 15; 2/59
[58] Field of Search ................. 128/82, 165, 169, 171, 128/DIG. 15, 157; 2/240, 59, DIG. 6; 36/8.1, 7.3, 7.1

[56] References Cited

U.S. PATENT DOCUMENTS

| 1,577,630 | 3/1926 | Yerger | 2/59 |
|---|---|---|---|
| 1,980,486 | 11/1934 | King et al. | 36/8.1 X |
| 2,229,575 | 1/1941 | Kaplan | 128/82 X |
| 3,245,406 | 4/1966 | Chardack | 128/171 X |
| 3,297,026 | 1/1967 | Van Pelt | 128/DIG. 15 |
| 3,324,580 | 6/1967 | Baxter | 36/8.1 |
| 3,657,741 | 4/1972 | Blanco | 2/59 |
| 3,747,125 | 7/1973 | Goldman et al. | 128/82 X |

*Primary Examiner*—John D. Yasko
*Attorney, Agent, or Firm*—Walter F. Jewell

[57] ABSTRACT

A protective device is provided for use on body members, e.g., bandaged or injured portions of the trunk and limbs. It provides a water-proof protection for the affected parts of the body and comprises generally a flexible tubular member having a fastening means affixed at one or both ends.

10 Claims, 5 Drawing Figures

BODY MEMBER PROTECTIVE DEVICE

This invention relates to protective devices. In one particular aspect, it relates to protective devices used to cover body members.

Patients who have sustained an injury to the body trunk, e.g., thorax, abdomen, or limbs, e.g., arm or leg, or who have had the same surgically operated upon, frequently must keep the affected area enclosed with medicinal dressings for prolonged periods of time. During these time periods, it is often necessary for the patient to bath or be bathed and thus risk having the bandage wetted.

It is, therefore, an object of this invention to provide a water-proof protective device for use over body members. This and other objects of the invention will become apparent from the following detailed description and drawings wherein.

Broadly, this invention provides a protective device for use on body members, e.g., bandaged trunk or limbs, comprising a flexible tubular body member enclosing means having at least one body member securing means. The member securing means comprises a foam-like cushionable band fixedly mounted, e.g., adhesively mounted, upon the exterior surface of one end of the tubular member and having a non-adhered overlapping portion in excess of the circumference of the tubular member. A flexible collar is fixedly mounted upon the cushionable band and the overlapping portion thereof. A body member-fastening means is fixedly secured to the cushionable band with the fastening means adapted to secure the protective device about the body member to be protected. In a preferred embodiment of this invention, the fastening means comprises a plurality of flexible plastic hooks and loops. The hooks may be fixedly mounted upon the overlapping portion of the cushionable material and the hook engaging loops may be fixedly mounted upon the cushionable material beneath the overlapping portion, or the position of the hooks and loops may be reversed.

The tubular limb enclosing member and the flexible collar may be made of thermoplastic material, such as polyvinylchloride, polyethylene, polypropylene, and the like. The cushionable band may be made of an absorbant foamable plastic, such as polyurethane, and the like.

In the practice of this invention, the protective device may be shaped into any desired form for enclosing a body member. For example, the tubular member may be shaped in the form of a foot, hand, or other body member including the chest and abdoment.

Figure 1:
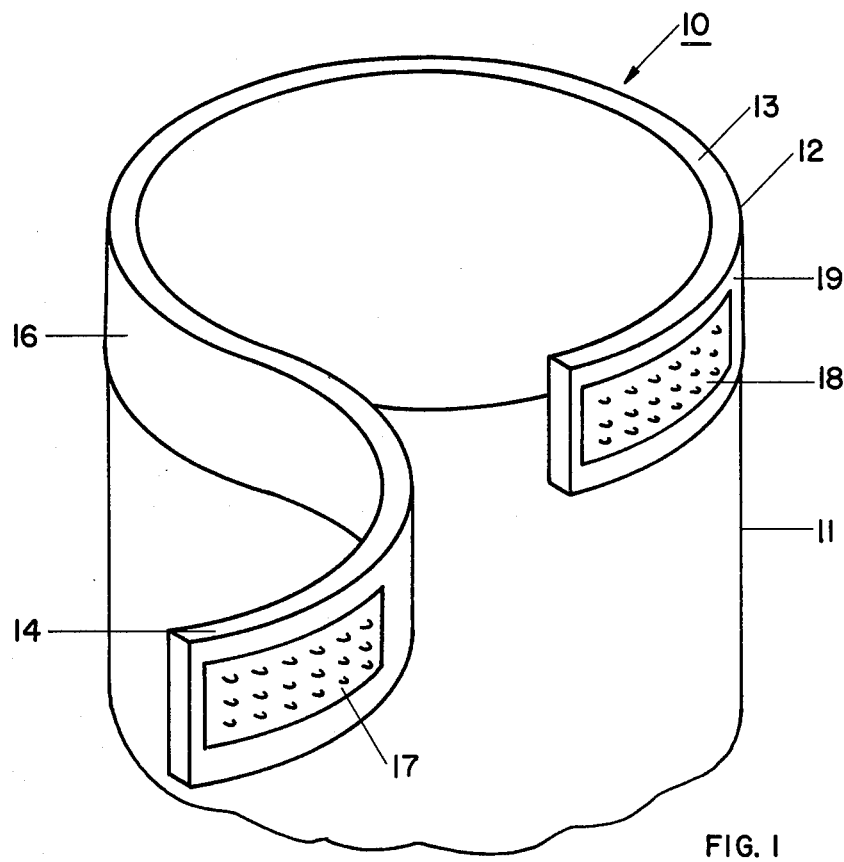
FIG. 1 is a prospective view of the protective device of this invention showing the limb securing means.

Referring now to FIG. 1, there is shown generally at 10 a protective device of this invention, comprising a flexible-tubular body member enclosing means 11 and a member securing means 12. The member securing means 12 comprises a foam cushionable material 13 fixedly mounted, e.g., adhesively mounted, upon the tubular member 11 having a non-adhered portion 14, which portion is in excess of the circumference of the flexible tube 11. The cushionable material 13 has a flexible collar 16 fixedly mounted to the exterior surface thereof. On the interior surface of the cushionable portion 13 fastening means consist of hooks 17 and loops 18. The loops are mounted upon the exterior surface of the collar 16 and the hooks 17 are mounted on the surface of the cushionable portion 13, which overlaps the circumference of the tube 11, as noted above, the positions of the hooks and loops may be reversed. To engage the hooks 17 and the loops 18, the overlapping portion 14 is brought in alignment with the loop section 19 and the two surfaces are pressed together, thus engaging the hooks 17 and the loops 18. Disengagement is brought about by pulling apart the hook and loop sections.

Figure 2:
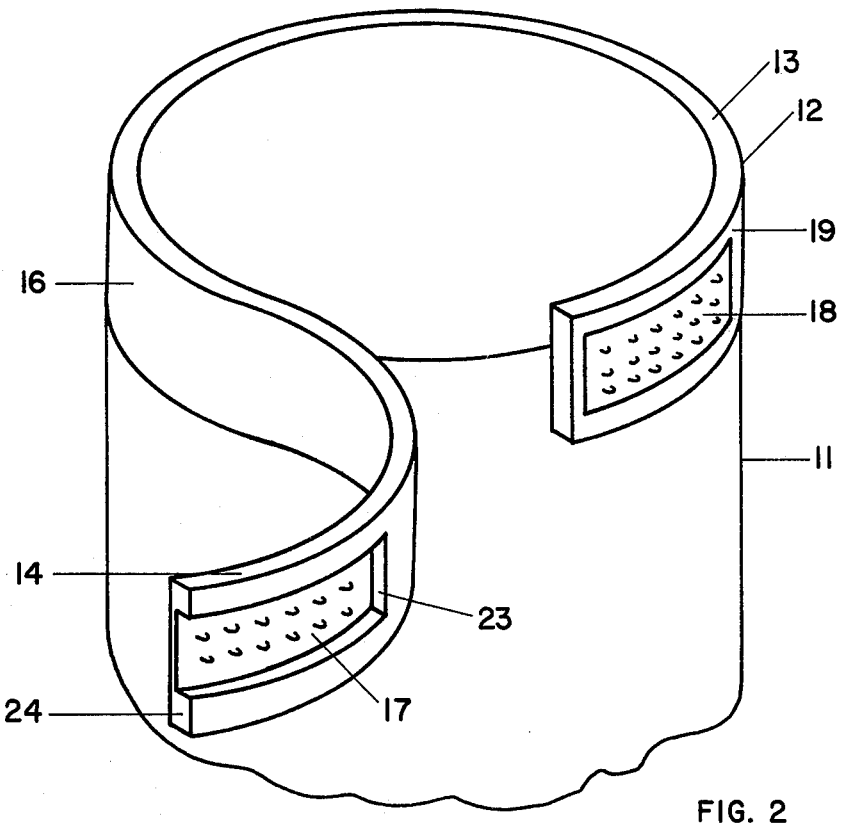
FIG. 2 is a prospective view of an embodiment of the device of FIG. 1.

In an embodiment of this invention, the hook 17 or loop 18 sections may be recessed to provide a better closure for the body member securing means. As shown in FIG. 2, the non-adhered portion 14 of the cushionable material 13 is a recessed section 23, which is open at the end 24 of the cushionable material 13. As illustrated, the hook 17 portion is within the recess 23. When the hooks 17 are engaged with the loops 18 (as described above) the interior non-recessed surface of the cushionable material 13 is flush with the collar 19.

While the fastening means of this invention have been described in the terms of hooks and loops, it is understood by those skilled in the art that other fastening means may be used, such as snaps or a series of belt-like retaining loops in which the overlapping portion 14 may be inserted.

Figure 3:
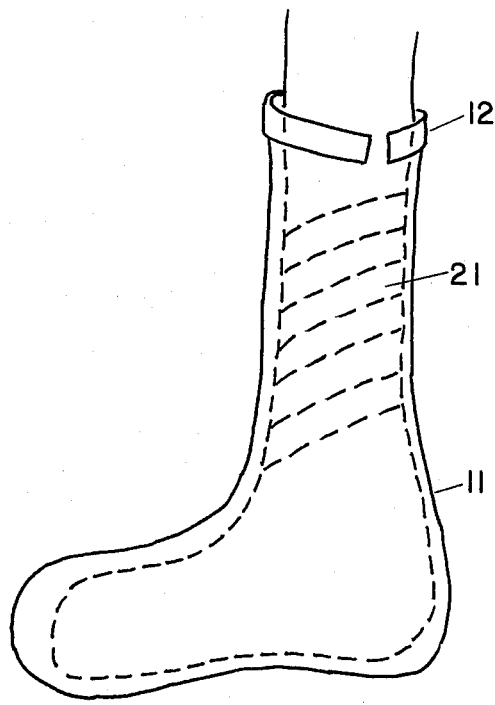
FIG. 3 is a view illustrating the device of FIG. 1 in position on a bandaged leg.
Figure 4:
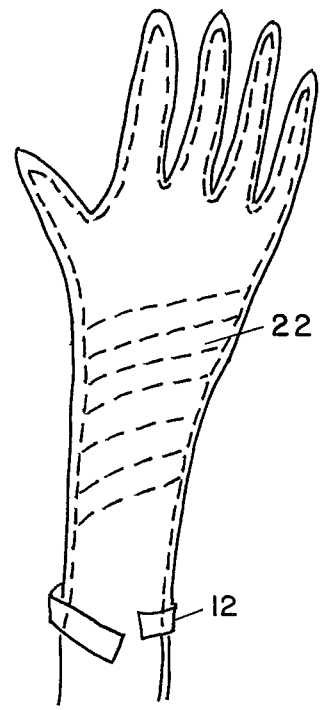
FIG. 4 is a view illustrating the device of FIG. 1 in position on a bandaged arm.

FIGS. 3 and 4 illustrate two additional embodiments of the invention. In FIG. 3, a bandaged foot 21 is shown enclosed by a foot-shaped limb enclosing member 11 having a limb securing means 12. In FIG. 4, a bandaged arm is illustrated, showing the bandaged portion 22 and a handshaped limb enclosing member 11 having a fastening means 12.

Figure 5:
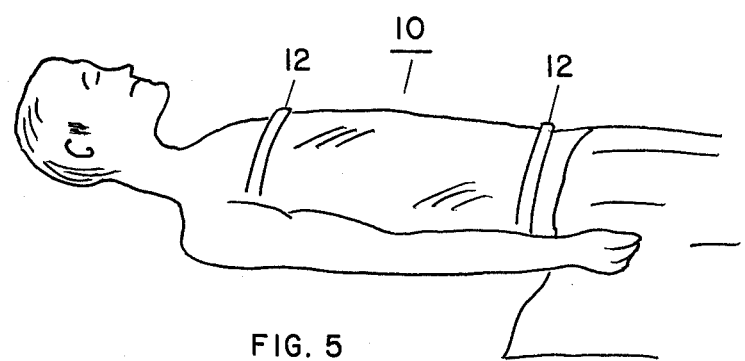
FIG. 5 is a view illustrating the device of FIG. 1 in position on the thorax and abdomen of a patient.

Another aspect of this invention concerns the use of the protective device to act as a self-sealing window dressing in those cases where it is important that the likelihood of outside bacterial infection be decreased. This would be particularly advantageous to patients who receive severe burns. In such cases, the affected area is required to be maintained in a sterilized condition for a long period of time. By employing clear plastic in the protective device of this invention. Doctors would be able to view the condition of the particular wound without necessarily removing the dressing (See FIG. 5).

It is a further aspect of this invention that traditional surgical dressings may be affixed to the interior of the protective device so as to maximize sealed conditions when required. The protective device may also be perforated to permit the passage of air when necessary for the healing process.

Although the detailed description of the protective device of this invention has been described with only one body member securing means, it is understood that two such securing means are within the scope of this invention when the device is used as a sleeve about a body member.

What is claimed is:

1. In a protective device comprising a flexible tubular body member enclosing means having at least one body member securing means comprising a foam-like cushionable band fixedly mounted upon the exterior surface of one end of the tubular member and having a non-adhered overlapping portion in excess of the circumference of the tubular member, a flexible collar fixedly mounted upon the cushionable band and the overlapping portions thereof, and a body member fastening means adapted to secure the protective device about the body member to be protected, the fastening means comprising a plurality of flexible hooks fixedly mounted upon the overlapping portion of the cushionable material and a plurality of flexible hook engaging loops fixedly mounted upon the cushionable material beneath the overlapping portion, the hooks and loops adapted for rapid and easy engagement and disengagement, the improvement which comprises fixedly mounting the flexible hooks in a recessed section of the overlapping portion of the cushionable material.

2. The protective device of claim 1, wherein the non-fastening end of the body member enclosing member is sealed and is adapted to enclose the exterior of the body member to be protected.

3. The protective device of claim 1, wherein both ends of the protective device have a body member securing means.

4. The protective device of claim 1, wherein the tubular body member enclosing means and the collar is made of a thermoplastic material selected from the group consisting of polyvinylchloride, polyethylene, polypropylene, and the like.

5. The protective device of claim 1, wherein the cushionable band is made of polyurethane.

6. In a protective device comprising a flexible tubular body member enclosing means having at least one body member securing means comprising a foam-like cushionable band fixedly mounted upon the exterior surface of one end of the tubular member and having a non-adhered overlapping portion in excess of the circumference of the tubular member, a flexible collar fixedly mounted upon the cushionable band and the overlapping portions thereof, and a body member fastening means adapted to secure the protective device about the body member to be protected, the fastening means comprising a plurality of flexible hooks engaging loops fixedly mounted upon the overlapping portion of the cushionable material and a plurality of flexible hooks fixedly mounted upon the cushionable material beneath the overlapping portion, the hooks and loops adapted for rapid and easy engagement and disengagement, the improvement which comprises fixedly mounting the flexible loops in a recessed section of the overlapping portion of the cushionable material.

7. The protective device of claim 5, wherein the non-fastening end of the body member enclosing member is sealed and is adapted to enclose the exterior of the body member to be protected.

8. The protective device of claim 5, wherein both ends of the protective device have a body member securing means.

9. The protective device of claim 5, wherein the tubular body member enclosing means and the collar is made of a thermoplastic material selected from the group consisting of polyvinylchloride, polyethylene, polypropylene, and the like.

10. The protective device of claim 5, wherein the cushionable band is made of polyurethane.

* * * * *